(12) United States Patent
Lee et al.

(10) Patent No.: US 9,303,278 B2
(45) Date of Patent: Apr. 5, 2016

(54) MUTANT L-ARABITOL DEHYDROGENASE DERIVED FROM NEUROSPORA CRASSA WITH ENHANCED ACTIVITY

(71) Applicant: Konkuk University Industrial Cooperation Corp., Seoul (KR)

(72) Inventors: Jung Kul Lee, Seoul (KR); Hee Jung Moon, Seoul (KR); Manish Kumar Tiwari, Seoul (KR); Tae Su Kim, Seoul (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 14/364,631

(22) PCT Filed: Apr. 18, 2013

(86) PCT No.: PCT/KR2013/003317
§ 371 (c)(1),
(2) Date: Jun. 11, 2014

(87) PCT Pub. No.: WO2013/168908
PCT Pub. Date: Nov. 14, 2013

(65) Prior Publication Data
US 2014/0370554 A1 Dec. 18, 2014

(30) Foreign Application Priority Data
May 10, 2012 (KR) .......................... 10-2012-0049433

(51) Int. Cl.
C12N 9/04 (2006.01)
C12P 19/02 (2006.01)

(52) U.S. Cl.
CPC .............. *C12P 19/02* (2013.01); *C12N 9/0006* (2013.01); *C12Y 101/01012* (2013.01)

(58) Field of Classification Search
None
See application file for complete search history.

(56) References Cited

FOREIGN PATENT DOCUMENTS

KR 10-2001-0049616 6/2001

OTHER PUBLICATIONS

Nishikawa et al., "Two Histidine Residues are Essential for Ribonuclease T1 Activity as is the Case for Ribonuclease A", Biochemistry 26:8620-8624, 1987.*
Tiwari et al., "Molecular modeling studies of L-arabinitol 4-dehydrogenase of Hypocrea jecorina: Its binding interactions with substrate and cofactor", J. Mol. Graphics Model. 28:707-713, 2010.*
Tiwari et al., "Information for Molecular modeling studies of L-arabinitol 4-dehydrogenase of Hypocrea jecorina: its binding interactions with substrate and cofactor", 6 pages, 2010.*
Mayahi et al., Cir. Cardiovasc. Genet. 3:513-522, 2010.*
Tiwari et al., "Role of Conserved Glycine in Zinc-dependent Medium Chain Dehydrogenase/Reductase Superfamily", J. Biol. Chem. 287:19429-19439, Apr. 12, 2012.*
Airaksinen et al., "Modified base compositions at degenerate positions of a mutagenic oligonucleotide enhance randomness in site-saturation mutagenesis", Nucleic Acids Res. 26:576-581, 1998.*
Rutten et at, "A Single amino acid change (Y318F) in the L-arabitol dehydrogenase (LadA) from Asperigillus niger results in a significant increase in affinity for D-sorbitol," BMC Microbiology, Aug. 2009.
Bae et al., "Structure and Engineering of L-Arabinitol 4-Dehydrogenase from Neurospora crassa," Applied Microbiology and Biotechnology, Jul. 2010.
Sullivan et al., "Cloning, characterization, and mutational analysis of highly active and stable L-arabinitol 4-dehydrogenase from Neurospora crassa," Applied Microbiology and Biotechnology, Oct. 2007.
Kim et al., Cloning, characeterization, and engineering of fungal L-arabinitol dehydrogenases, Applied Microbiology and Biotechnology, Applied Microbiology and Biotechnology, Apr. 2010.
De Groot et al., "Regulation of Pentose Catabolic Pathway Genes of Asperigillus niger," Food Technology and Biotechnology, Dec. 2006.
Suzuki et al., "Cloning and Expression of NAD+-Dependent L-Arabinitol 4-Dehydrogenase Gene (ladA_of Aspergillus oryzae," Journal of Bioscience and Bioengineering, Jun. 2005.

* cited by examiner

*Primary Examiner* — David J Steadman
(74) *Attorney, Agent, or Firm* — Baker & Hostetler LLP

(57) ABSTRACT

The present invention is to enhance the stability and enzyme activity of an L-arabitol dehydrogenase derived from *Neurospora crassa* using techniques from quantum mechanics and molecular mechanics and partial mutation techniques. More specifically, the present invention relates to a method for preparing an L-arabitol dehydrogenase in which a residue which affects enzyme stability is found through a screening based on quantum mechanics and molecular mechanics, and enzyme activity is enhanced by mutation of the found residue, nucleic acid molecules encoding the L-arabitol dehydrogenase, a vector including the nucleic acid molecules, a transformant including the vector, a mutant of the L-arabitol dehydrogenase and an improved L-arabitol dehydrogenase.

1 Claim, 5 Drawing Sheets

MUTANT L-ARABITOL DEHYDROGENASE DERIVED FROM NEUROSPORA CRASSA WITH ENHANCED ACTIVITY

CROSS-REFERENCE TO RELATED APPLICATIONS

This application is a U.S. national stage application of International Application No. PCT/KR2013/003317, filed Apr. 18, 2013, which claims the benefit of Korean Patent Application KR10-2012-0049433, filed on May 10, 2012, both of which are incorporated by reference herein in their entirety.

TECHNICAL FIELD

The present invention is to enhance an enzyme activity of an L-arabitol dehydrogenase derived from *Neurospora crassa* by using molecular mechanics and site-specific mutation techniques. More specifically, the present invention relates to an L-arabitol dehydrogenase of which an enzyme activity is enhanced by a mutation, a nucleic acid molecule encoding the same, a vector including the nucleic acid molecule, a transformant including the vector, a mutant of the L-arabitol dehydrogenase, and a method for preparing the improved L-arabitol dehydrogenase.

BACKGROUND

Recently, as uses of L-carbohydrate and its nucleoside derivatives are greatly increased in a medical field, a modified nucleoside exhibits a significant potential as a useful anti-virus agent. L-xylulose is a core pentose which constitutes a framework in synthesizing L-ribonucleoside, L-oligoribonucleoside and many agents for use in the treatment. Since L-nucleoside has a high stability from an attack of nucleases, and the like, in a body, when comparing it with D-nucleoside, it is a high potential candidate material which can be used as a material for use in the treatment. Since L-ribose is recently more focused as it is known to have a high usefulness as a raw material for preparing a medicine such as an anti-virus agent, anti-cancer agent, and the like, it is needed to establish a high efficient biological method for preparing L-xylulose.

Despite the above importance and usefulness, xylose and xylulose produced from hydrolysis of plant materials have disadvantages such as a high price, a high production cost, and the like. The hydrolysis treatment of the plant materials results in a low yield and low purity, the acid and material used in the hydrolysis have to be removed by an ion exchange treatment after the hydrolysis treatment, and requires a further purification to be suitable for a food. Such ion exchange and crystalization treatments lead to an increase of the production cost. Therefore, a method for biochemically producing L-xylulose from L-arabitol by using a microorganism and its enzyme has been attemped (Suzuki, T., Tran, L. H., Yoqo, M., Idota, O., Kitamoto, N., Kawai, K., Takamizawa, K. (2005) J. Biosci. Bioeng. 100 (4), 472-474), it is expected that the enzymatic production method for producing L-xylulose by using biocatalysts can overcome the disadvantages. Unlike D-xylulose, since L-xylulose is present in a little amount in the nature, and also has low enzyme stability and enzyme activity, it is difficult to industrialize it (Sullivan, R., Zhao, H. (2007) Appl. Microbiol. Biotechnol., 77, 845-852). Therefore, the enzymatic production method for producing L-xylulose using biocatalysts should secure the enzyme stability and the high enzyme activity.

SUMMARY

The present invention is derived by said requirement and the object of the present invention is to improve the enzyme activity via site-specific mutation techniques in order to utilize L-arabitol dehydrogenase which functions to a bioconversion of a functional sugar, L-xylulose, as an enzyme for a practical use in the industry.

The second object of the present invention is to provide a recombinant expression vector including the improved L-arabitol dehydrogenase gene.

The third object of the present invention is to provide all transformant strains including a recombinant *E. coli* in which the improved gene is transformed.

The fourth object of the present invention is to provide a recombinant ribitol dehydrogenase using the recombinant *E. coli* in which the improved gene is transformed.

The fifth object of the present invention is to prove residues affecting the activity of L-arabitol dehydrogenase using the enzyme.

Technical Solution

In order to achieve the objects, the present invention provides a mutant L-arabitol dehydrogenase selected from a group consisting of a mutant in which histidine, an amino acid at the position 58 is substituted with alanine; a mutant in which proline, an amino acid at the position 104 is substituted with alanine; a mutant in which isoleucine, an amino acid at the position 191 is substituted with alanine or valine; a mutant in which isoleucine, an amino acid at the position 282 is substituted with leucine; and a mutant in which glutamine, an amino acid at the position 306 is substituted with alanine, in the sequence of L-arabitol dehydrogenase having SEQ ID NO: 3.

In one embodiment of the present invention, the enzyme is preferably derived from *Neurospora crassa*, but L-arabitol dehydrogenase made by chemical synthesis or genetic engineering methods is also included in the scope of the present invention.

In another embodiment of the present invention, the mutant enzymes preferably have amino acids of SEQ ID NOs: 5, 7, 9, 11, 13 and 15 but mutants having the effect intended to be achieved by the present invention through one or more of a substitution, deletion, inversion, translocation, and the like, are also included in the present invention.

In addition, the present invention provides a gene encoding the enzyme of the present invention.

In one embodiment of the present invention, said genes preferably have base sequences of SEQ ID NOs: 6, 8, 10, 12, 14 and 16 but mutants having the effect intended to be achieved by the present invention through one or more substitution, deletion, inversion, translocation, and the like, to the sequences are also included in the present invention.

Also, the present invention provides recombinant vectors comprising above-mentioned genes of the present invention.

The present invention provides a method for preparing said mutant enzymes of the present invention, which comprises steps of transforming the recombinant vectors of the present invention into a microorganism to prepare transformants, and expressing the enzymes of the present invention.

Also, the present invention can be used in enhancing the productivity of L-xylulose from L-arabitol by using the mutants of the present invention.

Hereinafter, the present invention will be described.

The present invention provide a basic technique for identifying a determinant of dehydrogenase activity, by presenting the important residue which can regulate an enzyme activity of the L-arabitol dehydrogenase.

Further, the present invention provides a high active L-arabitol dehydrogenase using the mutant L-arabitol dehydrogenase of the present invention, which can be used in efficiently producing L-xylulose.

Hereinafter, the present invention will be described in detail.

SEQ ID NOs: 6, 8, 10, 12, 14 and 16 represent base sequences of the mutated L-arabitol dehydrogenase genes of the present invention, SEQ ID NOs: 5, 7, 9, 11, 13 and 15 represent amino acid sequences encoded by the genes. As described above, variations such as a deletion, substitution, addition, and the like, for several amino acids can be present, as long as polypeptides having the amino acid sequences have L-arabitol dehydrogenase activity. In addition, genes of the present invention comprise ones having base sequences encoding amino acids which are represented by SEQ ID NOs: 6, 8, 10, 12, 14 and 16, as well as a degeneracy isomer which encodes the same polypeptide but is different only in the degeneracy codon. Wherein the variation such as the deletion, substitution, addition, and the like, can be introduced by site-directed mutagenesis method (Current Protocols in Molecular Biology Volume 1, page 811, 1994), and the like.

The transformed microorganisms of the present invention can be obtained by introducing the recombinant vectors of the present invention into a host which is suitable for the expression vectors used in the preparation of the recombinant vectors. For example, when bacteria such as E. coli, and the like, are used as the host, the recombinant vector of the present invention is preferably one having constitution necessary for the expression, such as a promoter, DNA comprising L-arabitol dehydrogenase gene, transcription terminator sequence, and the like, while the vector itself is able to autonomously replicate in the host. pET-28a is used as the expression vector used in the present invention but any one of the expression vectors satisfying said requirements can be used.

As the promoter, any promoter can be used if it can be expressed in the host, and for example, the promoters derived from E. coli or phage, and the like, such as tip promoter, trc promoter, tac promoter, lac promoter, PL promoter, PR promoter, T7 promoter, T3 promoter, and the like, can be used. As the method for introducing the recombinant DNA into bacteria, the calcium chloride method or electroporation method, and the like, as mentioned above, is available.

In addition, the recombinant vectors which further have fragments having many kinds of functions for inhibiting, amplifying or inducing the expression, or genes encoding a marker for selecting a transformant, a resistant gene for antibiotic or a signal for the purpose of secreting out of the strain, and the like, can be used.

The preparation process of the mutated L-arabitol dehydrogenase of the present invention is conducted as follows. It can be practiced by transforming the host into the recombinant vector having gene encoding the mutated enzyme, culturing the transformant obtained above, producing and accumulating the gene product, L-arabitol dehydrogenase in the culture (the cultured mycobiont or the cultivation supernatant), and obtaining L-arabitol dehydrogenase from the culture.

As the method for cultivating the transformant of the present invention, any conventional method used in cultivating the host can be used.

Also, if the microorganism in which promoter is transformed by using the inducible expression vector is cultivated, the inducible materials suitable for the kinds of promoters is added to a medium. For example, isopropyl-D-thiogalatopyranoside (IPTG), kanamycin, and the like, can be mentioned as the inducible material.

An obtainment and purification of the mutated L-arabitol dehydrogenase can be made by recovering the mycobiont or the supernatant from the culture by centrifugation, and then by alone or properly combining the mycobiont fragmentation, extraction, affinity chromatography, cation or anion exchange chromatography, gel filtration, and the like.

The process for identifying the fact that the purified material as obtained is the desired enzyme can be made by the conventional methods, for example, SDS-polyacrylamide gel electrophoresis, western blotting, and the like.

In addition, the cultivation of the transformant using the microorganism as the host, the production of L-arabitol dehydrogenase by the transformant, the accumulation in the mycobiont, and the recovery of L-arabitol dehydrogenase from the mycobiont are not limited to the process.

The present invention cloned the gene for L-arabitol dehydrogenase from *Neurospora crassa* in order to obtain the high active enzyme and present several residues which play an important role in the activity of the enzyme. It was confirmed that the basic technique for identifying the high active determinant can be provided by presenting residues which play an important role in the high activity. The activity for converting from L-arabitol to L-xylulose could be increased by using the mutant enzyme obtained by mutating the residues which play an important role in enzyme activity.

In mutants in which residues which play an important role in the activity are substituted by using *Neurospora crassa*-derived L-arabitol dehydrogenase (NcLAD), obtained from the present invention, NcLAD H58A has $K_m$ value of 6.57 mM, $k_{cat}$ value of 3220 min$^{-1}$ for the substrate, NcLAD P104A has $K_m$ value of 3 mM, $k_{cat}$ value of 1320 min$^{-1}$ for the substrate, NcLAD I191A has $K_m$ value of 48.1 mM, $k_{cat}$ value of 4780 min$^{-1}$ for the substrate, NcLAD I191V has $K_m$ value of 6.07 mM, $k_{cat}$ value of 3940 min$^{-1}$ for the substrate, NcLAD I282L has $K_m$ value of 5.7 mM, $k_{cat}$ value of 3790 min$^{-1}$ for the substrate, NcLAD Q306A has $K_m$ value of 6.0 mM, $k_{cat}$ value of 1820 min$^{-1}$ for the substrate.

By using several L-arabitol dehydrogenase variants exhibiting the high activity in the present invention, the activity of the enzyme could be increased, simultaneously with increasing a binding force on the substrate. It will be usefully applied to the economic production of L-xylulose from a sugar mixture by overcoming the problems relating to the low enzyme activity of the existing L-arabitol dehydrogenase.

Effect

L-xylulose produced by L-arabitol dehydrogenase has the medically and pharmaceutically useful values, such as anti-virus agent, and the like, but has disadvantages such as the instability of the subject enzyme and low enzyme activity.

Therefore, the present invention relates to a development of the improved enzyme of which activity is increased, simultaneously with increasing the ability of the substrate to bind to the enzyme, by mutating residues which play an important role in the activity of L-arabitol dehydrogenase derived from *Neurospora crassa*. In addition, L-xylulose can be efficiently prepared by using the mutant of L-arabitol dehydrogenase and improved L-arabitol dehydrogenase.

DETAILED DESCRIPTION OF ILLUSTRATIVE EMBODIMENTS

Hereinafter, the present invention is described in detail by the following Examples, but it is not limited thereto.

EXAMPLE 1

Gene Cloning of L-arabitol Dehydrogenase

*Neurospora crassa* (ATCC Accession No. 10333, American Type Culture Collection, USA) were cultivated at 24° C., and centrifuged (8,000×g, 10 min) to obtain mycobiont. Genomic DNA was isolated from the obtained mycobiont, and primers, NcLAD F-5'-GTA GCT ACG TCA GAA TTC CAT GGC TTC TAG CGC TTC C-3' (SEQ ID NO: 1) NcLAD R-5'-GCT GAT TCT GCG GCC GCT TAC TCC AGA CTC TGG ATC-3' (SEQ ID NO: 2) were constructed by using the base sequence of the gene encoding L-arabitol dehydrogenase of *Neurospora crassa* and then PCR was conducted. PCR product, that is, a gene comprising L-arabitol dehydrogenase amplified in *Zymomonas mobilis* is inserted into pGEM T-easy vector and then analyzed for the base sequence (SEQ ID NO: 4).

EXAMPLE 2

Process for Preparing the Recombinant Expression Vector and the Recombinant Strain In order to largely express the former L-arabitol dehydrogenase in *E. coli* by using the gene encoding L-arabitol dehydrogenase according to Example 1, a gene of the enzyme was inserted between EcoRI and NotI sites of the expression vector, pET-28a (Novagen, Germany) and then transformed into *E. coli* BL21 (DE3) (NEB, England).

EXAMPLE 3

Expression and Pure Isolation of the Recombinant L-arabitol Dehydrogenase

Figure 1:
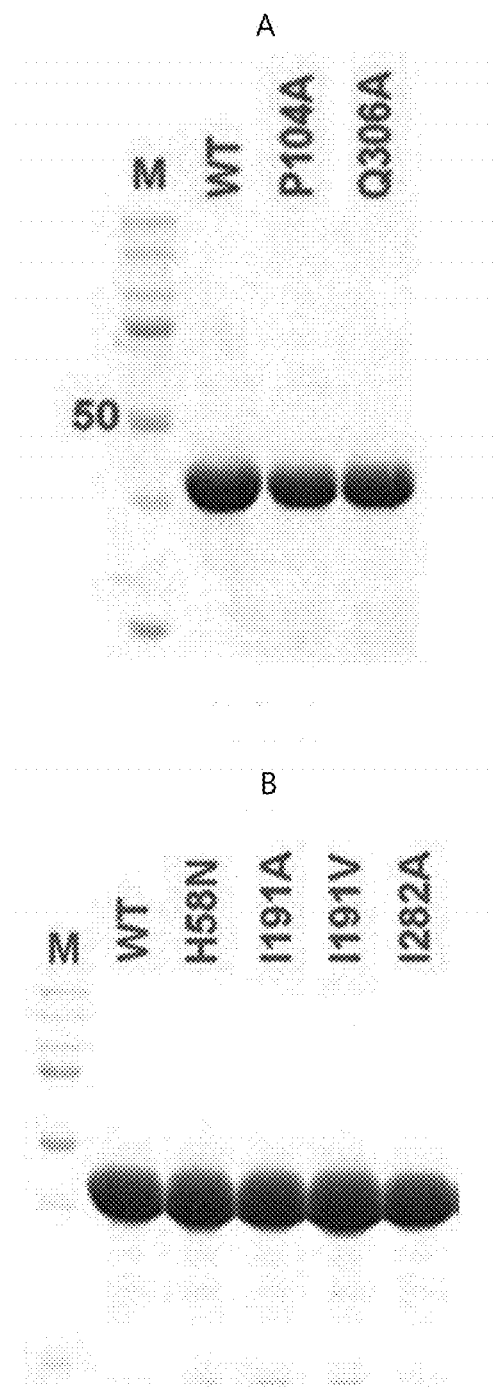
FIGS. 1A and 1B are photographs of SDS-polyacrylamide gel electrophoresis for wild-type L-arabitol dehydrogenase derived from *Neurospora crassa* strain and the high active variants, NcLAD H58A, P104A, I191A, I191V, I282L and NcLAD Q306A.

The recombinant strain prepared from Example 2 was inoculated to LB medium, cultured at 37° C. for 24 hours and then the expressed protein was identified on SDS-PAGE gel (FIG. 1).

In order to purify the recombinant L-arabitol dehydrogenase expressed by the process of the Example 3, after only collecting mycobiont from the recombinant strain culture by centrifugation (8,000×g, 10 minutes), the cell wall of *E. coli* was crushed by ultrasonic wave treatment, centrifuged it at 20,000×g for 20 minutes to remove a precipitation (mycobiont) and obtain a supernatant. A precipitant was removed by the centrifugation at 20,000×g for 20 minutes to obtain the supernatant, and then finally, subjected to a column chromatography using Ni-NTA Super flow column (GE Healthcare, England) to purely isolate the recombinant L-arabitol dehydrogenase.

EXAMPLE 4

Preparation of the Variant of L-arabitol Dehydrogenase Having a High Activity

EXAMPLE 4-1

Identification of Residues Playing an Important Role in the Activity

Figure 2:
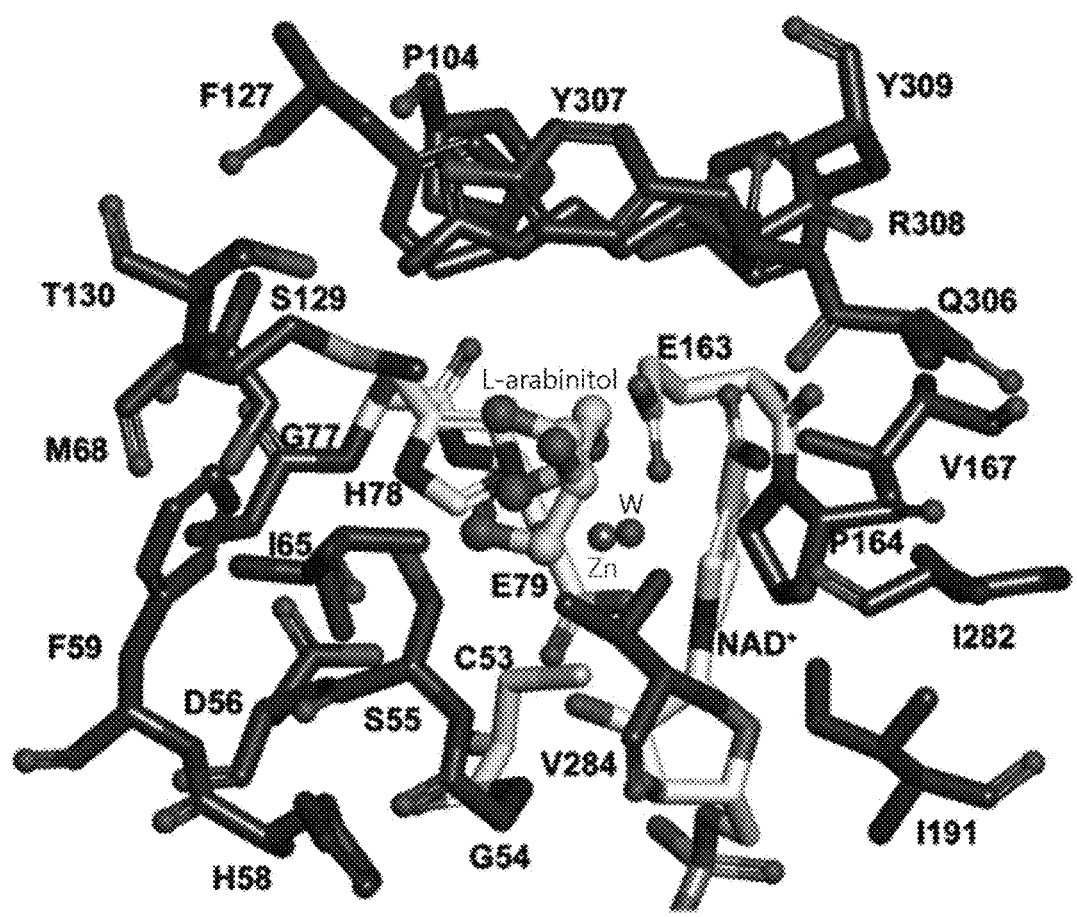
FIG. 2 illustrates a computer analysis for the active site to which the substrate of NcLAD binds, as analyzed by molecular mechanics basis.
Figure 3:
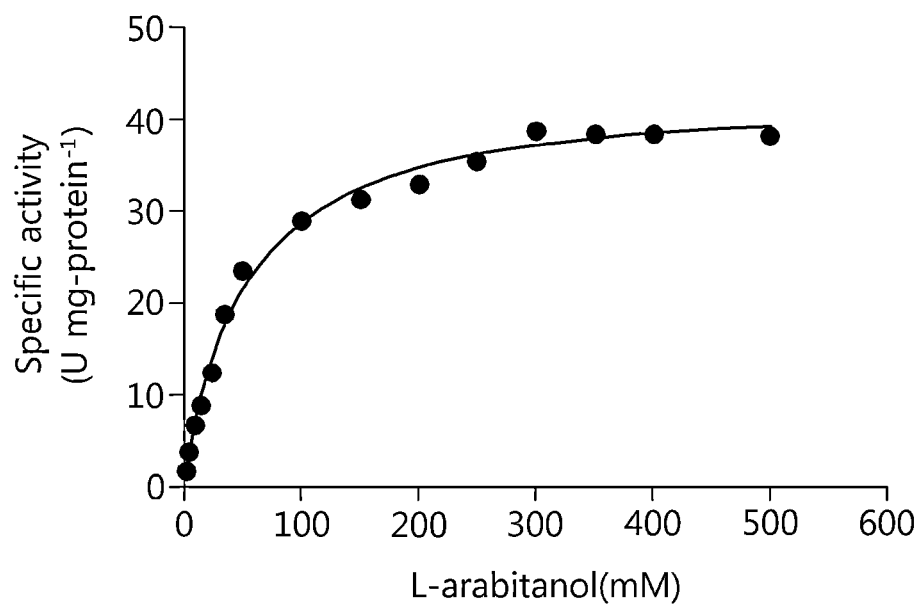
FIG. 3 illustrates a graph of dynamic parameters for the wild-type NcLAD enzyme.
Figure 4:
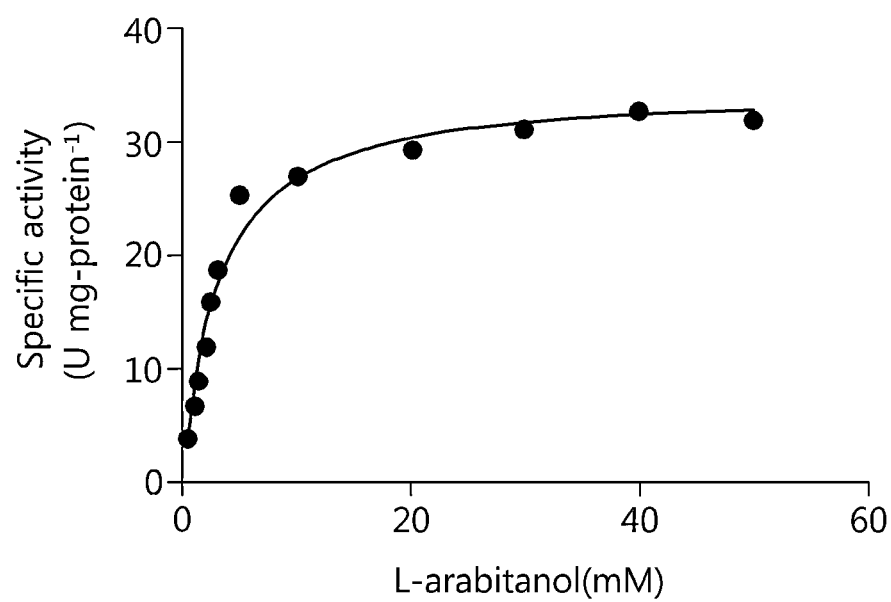
FIG. 4 illustrates a graph of dynamic parameters for NcLAD P104A variant.
Figure 5:
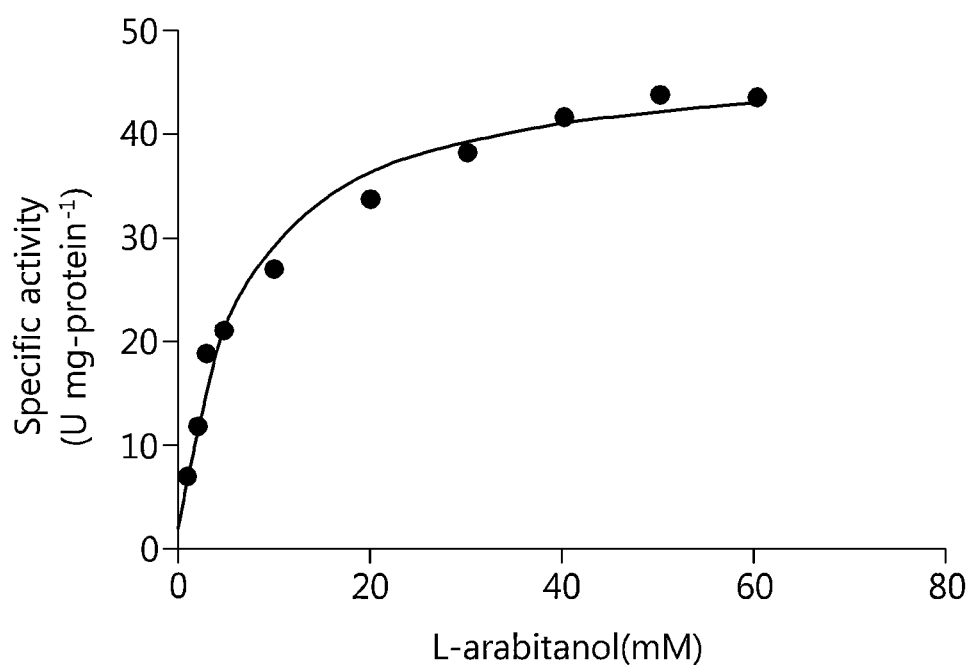
FIG. 5 illustrates a graph of dynamic parameters for NcLAD Q306A variant.

In order to search the residues which play an important role in the high activity by using L-arabitol dehydrogenase purely isolated from said Example 3, Quantum mechanics/Molecular mechanics techniques of Discovery Studio 3.1 and Meterials Studio 6.0 (Accelrys Inc. San Diego, Calif., USA) were used. The binding Energy (Kcal/mol) of the mutant in which residues of the substrate binding sites of the enzyme were substituted with alanine, as illustrated in FIG. 2 was compared with the binding Energy of the wild-type enzyme. It is known that the smaller the value of the binding Energy, the stronger the binding force. As illustrated in Table 1, the variant enzymes, H58A, P104A, I191A, I191V, I282L and Q306A had low binding Energy than that of wild-type enzymes, and H58, P104, I191, I282 and Q306 residues were selected as the object residues for the mutation.

TABLE 1

| Enzyme | A + B (Enzyme-Substrate complex) | A (Substrate) | B (Enzyme) | $BE_{QM}$ (Hartree) | Binding Energy (Kcal/mol) |
|---|---|---|---|---|---|
| WT | −12815.40 | −569.62 | −12245.7189 | −0.062 | −39.0 |
| P104A | −12738.67 | −569.62 | −12168.9862 | −0.065 | −40.75 |
| L165A | −13544.17 | −569.52 | −12974.8792 | 0.225 | 141.3 |
| I191A | −12628.70 | −569.62 | −12059.0203 | −0.066 | −41.9 |
| Q306A | −12608.94 | −569.62 | −12039.2535 | −0.068 | −42.8 |
| Y307A | −13544.17 | −569.31 | −12974.8792 | 0.025 | 15.9 |
| R308A | −13544.17 | −569.61 | −12974.5622 | 0.008156 | 5.1 |
| Y309A | −13544.17 | −569.22 | −12974.8792 | 0.005156 | 3.2 |
| H58A | −12592.10017 | −569.622357 | −12022.38216 | −0.095657 | −60.1 |
| I191V | −12698.57709 | −569.613965 | −12128.84528 | −0.117849 | −74.0 |
| I282L | −12698.42002 | −569.623466 | −12128.71014 | −0.086416 | −54.2 |

EXAMPLE 4-2

Dynamic Parameters of H58A, P104A, I191A, I191V, I282L, Q306A

As in Example 4-1, the residue representing low binding Energy in mutation among residues of substrate binding sites, histidine, the residue at the position of 58 was substituted with alanine; proline, the residue at the position of 104 was substituted with alanine; isoleucine, the residue at the position of 191 was substituted with alanine and valine; isoleucine, the residue at the position of 282 was substituted with leucine; glutamine, the residue at the position of 306 was substituted with alanine. The subject variants were prepared by using site-directed mutagenesis kit (Stratagene, USA), and it could be seen that the activities of Q306A variant, H58A variant, I191V variant and I282 variant as illustrated in Table 2, were increased, simultaneously with increasing the binding force on the substrates.

TABLE 2

| Enzyme | $K_m$ | | $k_{cat}$ (min$^{-1}$) $k_{cat}$ (min$^{-1}$) |
|---|---|---|---|
| | Coenzyme (μM) | Substrate (mM) | |
| NcLAD$_{WT}$ | 0.9 | 16.3 | 1600 |
| P104A | 0.9 | 3.0 | 1320 |
| L165A | ND | ND | ND |
| Q306A | 1.5 | 6.0 | 1820 |
| Y307A | ND | ND | ND |
| R308A | ND | ND | ND |
| Y309A | ND | ND | ND |
| H58A | 1.2 | 6.57 | 3220 |
| I191A | 1.4 | 48.1 | 4780 |
| I191V | 1.3 | 6.07 | 3940 |
| I282L | 1.7 | 5.7 | 3790 |

What is claimed is:

1. A mutant L-arabitol dehydrogenase consisting of the amino acid sequence as set forth in SEQ ID NO:13.

* * * * *

SEQUENCE LISTING

```
<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
gtagctacgt cagaattcca tggcttctag cgcttc                              36

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
gctgattctg cggccgctta ctccagactc tggatc                              36

<210> SEQ ID NO 3
<211> LENGTH: 363
<212> TYPE: PRT
<213> ORGANISM: Neurospora crassa

<400> SEQUENCE: 3

Met Ala Ser Ser Ala Ser Lys Thr Asn Ile Gly Val Phe Thr Asn Pro
  1               5                  10                  15

Gln His Asp Leu Trp Ile Ser Glu Ala Ser Pro Ser Leu Glu Ser Val
                 20                  25                  30

Gln Lys Gly Glu Glu Leu Lys Glu Gly Glu Val Thr Val Ala Val Arg
             35                  40                  45

Ser Thr Gly Ile Cys Gly Ser Asp Val His Phe Trp Lys His Gly Cys
         50                  55                  60

Ile Gly Pro Met Ile Val Glu Cys Asp His Val Leu Gly His Glu Ser
 65                  70                  75                  80

Ala Gly Glu Val Ile Ala Val His Pro Ser Val Lys Ser Ile Lys Val
                 85                  90                  95

Gly Asp Arg Val Ala Ile Glu Pro Gln Val Ile Cys Asn Ala Cys Glu
            100                 105                 110
```

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ile Gly
                180                 185                 190

Leu Ile Thr Met Leu Cys Ala Lys Ala Ala Gly Ala Cys Pro Leu Val
            195                 200                 205

Ile Thr Asp Ile Asp Glu Gly Arg Leu Lys Phe Ala Lys Glu Ile Cys
            210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ile Trp Ala
                260                 265                 270

Val Lys Phe Gly Gly Lys Val Phe Val Ile Gly Val Gly Lys Asn Glu
            275                 280                 285

Ile Gln Ile Pro Phe Met Arg Ala Ser Val Arg Glu Val Asp Leu Gln
            290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
                340                 345                 350

Gly Ala Ile Lys Val Gln Ile Gln Ser Leu Glu
            355                 360

<210> SEQ ID NO 4
<211> LENGTH: 1092
<212> TYPE: DNA
<213> ORGANISM: Neurospora crassa

<400> SEQUENCE: 4
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc cccaagtcat ctgcaatgcc tgcgagccct gcctgactgg ccgttacaac     360
ggatgcgagc gcgttgactt cctctctacg ccccctgtgc ccggccttct ccgccgctac     420
gttaaccacc ctgccgtgtg gtgccacaaa atcggtaaca tgtcctatga aaacggtgcc     480
atgctcgagc ccctttccgt ggcgctggcc ggtcttcaga gagccggtgt cgtctgggc     540 gaccctgtcc tcatctgtgg tgccggcccc attggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720

```
gccaagaaga tcgtcgagag ctttggtgga atcgagcccg cggtggctct cgagtgtact    780
ggtgtcgaga gcagtatcgc ggctgctatc tgggccgtca agttcggcgg caaggtgttc    840
gtcatcggcg tgggcaagaa cgagatccag attcctttca tgcgcgccag tgtgcgcgag    900
gtcgacctgc agttccagta ccgttactgc aacacttggc ccagggccat tcgcctggtc    960
gagaatggcc tcgttgacct caccaggctg gtgacgcacc gtttcccgtt ggaggatgcg   1020
ctcaaggcgt tcgagacggc gtcagacccc aagacgggtg ccatcaaggt gcagatccag   1080
agtctggagt aa                                                       1092
```

<210> SEQ ID NO 5
<211> LENGTH: 363
<212> TYPE: PRT
<213> ORGANISM: Artificial Sequence
<220> FEATURE:
<223> OTHER INFORMATION: Mutant

<400> SEQUENCE: 5

```
Met Ala Ser Ser Ala Ser Lys Thr Asn Ile Gly Val Phe Thr Asn Pro
 1               5                  10                  15

Gln His Asp Leu Trp Ile Ser Glu Ala Ser Pro Ser Leu Glu Ser Val
            20                  25                  30

Gln Lys Gly Glu Glu Leu Lys Glu Gly Glu Val Thr Val Ala Val Arg
        35                  40                  45

Ser Thr Gly Ile Cys Gly Ser Asp Val His Phe Trp Lys His Gly Cys
    50                  55                  60

Ile Gly Pro Met Ile Val Glu Cys Asp His Val Leu Gly His Glu Ser
65                  70                  75                  80

Ala Gly Glu Val Ile Ala Val His Pro Ser Val Lys Ser Ile Lys Val
                85                  90                  95

Gly Asp Arg Val Ala Ile Glu Ala Gln Val Ile Cys Asn Ala Cys Glu
            100                 105                 110

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ile Gly
            180                 185                 190

Leu Ile Thr Met Leu Cys Ala Lys Ala Ala Gly Ala Cys Pro Leu Val
        195                 200                 205

Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ala Ile Trp Ala
            260                 265                 270

Val Lys Phe Gly Gly Lys Val Phe Val Ile Gly Val Gly Lys Asn Glu
        275                 280                 285
```

Ile Gln Ile Pro Phe Met Arg Ala Ser Val Arg Glu Val Asp Leu Gln
    290             295                 300

Phe Gln Tyr Arg Tyr Cys Asn Thr Trp Pro Arg Ala Ile Arg Leu Val
305             310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
            340                 345                 350

Gly Ala Ile Lys Val Gln Ile Gln Ser Leu Glu
            355                 360

<210> SEQ ID NO 6
<211> LENGTH: 1092
<212> TYPE: DNA
<213> ORGANISM: Artificial Sequence
<220> FEATURE:
<223> OTHER INFORMATION: mutant

<400> SEQUENCE: 6

```
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagg cccaagtcat ctgcaatgcc tgcgagccct gcctgactgg ccgttacaac     360
ggatgcgagc gcgttgactt cctctctacg cccctgtgc ccggccttct ccgccgctac      420
gttaaccacc ctgccgtgtg gtgccacaaa atcggtaaca tgtcctatga aacggtgcc      480
atgctcgagc cccttccgt ggcgctggcc ggtcttcaga gagccggtgt cgtctgggc       540
gaccctgtcc tcatctgtgg tgccggcccc attggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720
gccaagaaga tcgtcgagag ctttggtgga atcgagcccg cggtggctct cgagtgtact     780
ggtgtcgaga gcagtatcgc ggctgctatc tgggccgtca agttcggcgg caaggtgttc     840
gtcatcggcg tgggcaagaa cgagatccag attccttttca tgcgcgccag tgtgcgcgag     900
gtcgacctgc agttccagta ccgttactgc aacacttggc ccagggccat tcgcctggtc     960
gagaatggcc tcgttgacct caccaggctg gtgacgcacc gtttcccgtt ggaggatgcg    1020
ctcaaggcgt tcgagacggc gtcagacccc aagacgggtg ccatcaaggt gcagatccag    1080
agtctggagt aa                                                        1092
```

<210> SEQ ID NO 7
<211> LENGTH: 363
<212> TYPE: PRT
<213> ORGANISM: Artificial Sequence
<220> FEATURE:
<223> OTHER INFORMATION: mutant

<400> SEQUENCE: 7

Met Ala Ser Ser Ala Ser Lys Thr Asn Ile Gly Val Phe Thr Asn Pro
1               5                   10                  15

Gln His Asp Leu Trp Ile Ser Glu Ala Ser Pro Ser Leu Glu Ser Val
            20                  25                  30

```
Gln Lys Gly Glu Glu Leu Lys Glu Gly Val Thr Val Ala Val Arg
             35                  40                  45
Ser Thr Gly Ile Cys Gly Ser Asp Val His Phe Trp Lys His Gly Cys
 50                  55                  60
Ile Gly Pro Met Ile Val Glu Cys Asp His Val Leu Gly His Glu Ser
 65                  70                  75                  80
Ala Gly Glu Val Ile Ala Val His Pro Ser Val Lys Ser Ile Lys Val
                 85                  90                  95
Gly Asp Arg Val Ala Ile Glu Pro Gln Val Ile Cys Asn Ala Cys Glu
            100                 105                 110
Pro Cys Leu Thr Gly Arg Tyr Asn Gly Cys Glu Arg Val Asp Phe Leu
        115                 120                 125
Ser Thr Pro Pro Val Pro Gly Leu Leu Arg Arg Tyr Val Asn His Pro
130                 135                 140
Ala Val Trp Cys His Lys Ile Gly Asn Met Ser Tyr Glu Asn Gly Ala
145                 150                 155                 160
Met Leu Glu Pro Leu Ser Val Ala Leu Ala Gly Leu Gln Arg Ala Gly
                165                 170                 175
Val Arg Leu Gly Asp Pro Val Leu Ile Cys Gly Ala Gly Pro Ile Gly
            180                 185                 190
Leu Ile Thr Met Leu Cys Ala Lys Ala Ala Gly Ala Cys Pro Leu Val
        195                 200                 205
Ile Thr Asp Ile Asp Glu Gly Arg Leu Lys Phe Ala Lys Glu Ile Cys
210                 215                 220
Pro Glu Val Val Thr His Lys Val Glu Arg Leu Ser Ala Glu Glu Ser
225                 230                 235                 240
Ala Lys Lys Ile Val Glu Ser Phe Gly Gly Ile Glu Pro Ala Val Ala
                245                 250                 255
Leu Glu Cys Thr Gly Val Glu Ser Ser Ile Ala Ala Ile Trp Ala
            260                 265                 270
Val Lys Phe Gly Gly Lys Val Phe Val Ile Gly Val Gly Lys Asn Glu
        275                 280                 285
Ile Gln Ile Pro Phe Met Arg Ala Ser Val Arg Glu Val Asp Leu Gln
290                 295                 300
Phe Ala Tyr Arg Tyr Cys Asn Thr Trp Pro Arg Ala Ile Arg Leu Val
305                 310                 315                 320
Glu Asn Gly Leu Val Asp Leu Thr Arg Leu Val Thr His Arg Phe Pro
                325                 330                 335
Leu Glu Asp Ala Leu Lys Ala Phe Glu Thr Ala Ser Asp Pro Lys Thr
            340                 345                 350
Gly Ala Ile Lys Val Gln Ile Gln Ser Leu Glu
        355                 360

<210> SEQ ID NO 8
<211> LENGTH: 1092
<212> TYPE: DNA
<213> ORGANISM: Artificial Sequence
<220> FEATURE:
<223> OTHER INFORMATION: mutant

<400> SEQUENCE: 8
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
```

-continued

```
aagcatggtt gcatcggccc catgatcgtc gaatgcgatc atgtcctcgg ccacgagtcg    240
gcaggcgagg tcattgctgt ccatcccagc gtcaagagca tcaaggtcgg cgacagggtt    300
gccattgagc cccaagtcat ctgcaatgcc tgcgagccct gcctgactgg ccgttacaac    360
ggatgcgagc gcgttgactt cctctctacg ccccctgtgc ccggccttct ccgccgctac    420
gttaaccacc ctgccgtgtg gtgccacaaa atcggtaaca tgtcctatga gaacggtgcc    480
atgctcgagc ccctttccgt ggcgctggcc ggtcttcaga gagccggtgt tcgtctgggc    540
gaccctgtcc tcatctgtgg tgccggcccc attggtctga tcaccatgct ctgcgccaag    600
gccgctggtg cctgccctct tgtcattacc gacattgacg aaggccgctt gaagttcgcc    660
aaggagatct gccccgaggt cgtcacccac aaggtcgagc gcctgtcggc cgaggagtcg    720
gccaagaaga tcgtcgagag ctttggtgga atcgagcccg cggtggctct cgagtgtact    780
ggtgtcgaga gcagtatcgc ggctgctatc tgggccgtca agttcggcgg caaggtgttc    840
gtcatcggcg tgggcaagaa cgagatccag attcctttca tgcgcgccag tgtgcgcgag    900
gtcgacctgg ccttccagta ccgttactgc aacacttggc ccaggccat cgcctggtc    960 gagaatggcc tcgttgacct caccaggctg gtgacgcacc gtttcccgtt ggaggatgcg   1020
ctcaaggcgt tcgagacggc gtcagacccc aagacgggtg ccatcaaggt gcagatccag   1080
agtctggagt aa                                                      1092
```

<210> SEQ ID NO 9
<211> LENGTH: 363
<212> TYPE: PRT
<213> ORGANISM: Artificial Sequence
<220> FEATURE:
<223> OTHER INFORMATION: Mutant

<400> SEQUENCE: 9

```
Met Ala Ser Ser Ala Ser Lys Thr Asn Ile Gly Val Phe Thr Asn Pro
 1               5                  10                  15

Gln His Asp Leu Trp Ile Ser Glu Ala Ser Pro Ser Leu Glu Ser Val
            20                  25                  30

Gln Lys Gly Glu Glu Leu Lys Glu Gly Glu Val Thr Val Ala Val Arg
        35                  40                  45

Ser Thr Gly Ile Cys Gly Ser Asp Val Ala Phe Trp Lys His Gly Cys
    50                  55                  60

Ile Gly Pro Met Ile Val Glu Cys Asp His Val Leu Gly His Glu Ser
65                  70                  75                  80

Ala Gly Glu Val Ile Ala Val His Pro Ser Val Lys Ser Ile Lys Val
                85                  90                  95

Gly Asp Arg Val Ala Ile Glu Pro Gln Val Ile Cys Asn Ala Cys Glu
            100                 105                 110

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ile Gly
            180                 185                 190

Leu Ile Thr Met Leu Cys Ala Lys Ala Ala Gly Ala Cys Pro Leu Val
```

```
            195                 200                 205
Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ile Trp Ala
                260                 265                 270

Val Lys Phe Gly Gly Lys Val Phe Val Ile Gly Val Gly Lys Asn Glu
    275                 280                 285

Ile Gln Ile Pro Phe Met Arg Ala Ser Val Arg Glu Val Asp Leu Gln
    290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
                340                 345                 350

Gly Ala Ile Lys Val Gln Ile Gln Ser Leu Glu
                355                 360

<210> SEQ ID NO 10
<211> LENGTH: 1092
<212> TYPE: DNA
<213> ORGANISM: Artificial Sequence
<220> FEATURE:
<223> OTHER INFORMATION: Mutant

<400> SEQUENCE: 10
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt cgccttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc ccaagtcat ctgcaatgcc tgcgagccct gcctgactgg ccgttacaac     360
ggatgcgagc gcgttgactt cctctctacg cccctgtgc ccggccttct ccgccgctac     420
gttaaccacc tgccgtgtg gtgccacaaa atcggtaaca tgtcctatga gaacggtgcc     480
atgctcgagc cctttccgt ggcgctggcc ggtcttcaga gagccggtgt tcgtctgggc     540
gaccctgtcc tcatctgtgg tgccggcccc attggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720
gccaagaaga tcgtcgagag cttcggtgga atcgagcccg cggtggctct cgagtgtact     780
ggtgtcgaga gcagtatcgc ggctgctatc tgggccgtca agttcggcgg caaggtgttc     840
gtcatcggcg tgggcaagaa cgagatccag attcctttca tgcgcgccag tgtgcgcgag     900
gtcgacctgc agttccagta ccgttactgc aacacttggc cagggccat tcgcctggtc     960
gagaatggcc tcgttgacct caccaggctg gtgacgcacc gtttcccgtt ggaggatgcg    1020
ctcaaggcgt tcgagacggc gtcagacccc aagacgggtg ccatcaaggt gcagatccag    1080
agtctggagt aa                                                        1092
```

<210> SEQ ID NO 11
<211> LENGTH: 363
<212> TYPE: PRT
<213> ORGANISM: Artificial Sequence
<220> FEATURE:
<223> OTHER INFORMATION: Mutant

<400> SEQUENCE: 11

```
Met Ala Ser Ser Ala Ser Lys Thr Asn Ile Gly Val Phe Thr Asn Pro
  1               5                  10                  15

Gln His Asp Leu Trp Ile Ser Glu Ala Ser Pro Ser Leu Glu Ser Val
             20                  25                  30

Gln Lys Gly Glu Glu Leu Lys Glu Gly Glu Val Thr Val Ala Val Arg
         35                  40                  45

Ser Thr Gly Ile Cys Gly Ser Asp Val His Phe Trp Lys His Gly Cys
     50                  55                  60

Ile Gly Pro Met Ile Val Glu Cys Asp His Val Leu Gly His Glu Ser
 65                  70                  75                  80

Ala Gly Glu Val Ile Ala Val His Pro Ser Val Lys Ser Ile Lys Val
                 85                  90                  95

Gly Asp Arg Val Ala Ile Glu Pro Gln Val Ile Cys Asn Ala Cys Glu
            100                 105                 110

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ala Gly
            180                 185                 190

Leu Ile Thr Met Leu Cys Ala Lys Ala Ala Gly Ala Cys Pro Leu Val
        195                 200                 205

Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ala Ile Trp Ala
            260                 265                 270

Val Lys Phe Gly Gly Lys Val Phe Val Ile Gly Val Gly Lys Asn Glu
        275                 280                 285

Ile Gln Ile Pro Phe Met Arg Ala Ser Val Arg Glu Val Asp Leu Gln
    290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
            340                 345                 350

Gly Ala Ile Lys Val Gln Ile Gln Ser Leu Glu
        355                 360
```

<210> SEQ ID NO 12
<211> LENGTH: 1092
<212> TYPE: DNA
<213> ORGANISM: Artificial Sequence
<220> FEATURE:
<223> OTHER INFORMATION: Mutant

<400> SEQUENCE: 12

```
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc cccaagtcat ctgcaatgcc tgcgagcccc gcctgactgg ccgttacaac     360
ggatgcgagc gcgttgactt cctctctacg ccccctgtgc ccggccttct ccgccgctac     420
gttaaccacc tgccgtgtgt gtgccacaaa atcggtaaca tgtcctatga aacggtgcc      480
atgctcgagc ccctttccgt ggcgctggcc ggtcttcaga gagccggtgt cgtctctggc     540
gaccctgtcc tcatctgtgg tgccggcccc gccggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720
gccaagaaga tcgtcgagag ctttggtgga atcgagcccg cggtggctct cgagtgtact     780
ggtgtcgaga gcagtatcgc ggctgctatc tgggccgtca gttcggcgg caaggtgttc      840
gtcatcggcg tgggcaagaa cgagatccag attcctttca tgcgcgccag tgtgcgcgag     900
gtcgacctgc agttccagta ccgttactgc aacacttggc ccagggccat tcgcctggtc     960
gagaatggcc tcgttgacct caccaggctg gtgacgcacc gtttcccgtt ggaggatgcg    1020
ctcaaggcgt tcgagacggc gtcagacccc aagacgggtg ccatcaaggt gcagatccag    1080
agtctggagt aa                                                        1092
```

<210> SEQ ID NO 13
<211> LENGTH: 363
<212> TYPE: PRT
<213> ORGANISM: Artificial Sequence
<220> FEATURE:
<223> OTHER INFORMATION: Mutant

<400> SEQUENCE: 13

```
Met Ala Ser Ser Ala Ser Lys Thr Asn Ile Gly Val Phe Thr Asn Pro
  1               5                  10                  15

Gln His Asp Leu Trp Ile Ser Glu Ala Ser Pro Ser Leu Glu Ser Val
                 20                  25                  30

Gln Lys Gly Glu Glu Leu Lys Glu Gly Glu Val Thr Val Ala Val Arg
             35                  40                  45

Ser Thr Gly Ile Cys Gly Ser Asp Val His Phe Trp Lys His Gly Cys
         50                  55                  60

Ile Gly Pro Met Ile Val Glu Cys Asp His Val Leu Gly His Glu Ser
 65                  70                  75                  80

Ala Gly Glu Val Ile Ala Val His Pro Ser Val Lys Ser Ile Lys Val
                 85                  90                  95

Gly Asp Arg Val Ala Ile Glu Pro Gln Val Ile Cys Asn Ala Cys Glu
            100                 105                 110
```

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Val Gly
            180                 185                 190

Leu Ile Thr Met Leu Cys Ala Lys Ala Ala Gly Ala Cys Pro Leu Val
        195                 200                 205

Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ile Trp Ala
                260                 265                 270

Val Lys Phe Gly Gly Lys Val Phe Val Ile Gly Val Gly Lys Asn Glu
            275                 280                 285

Ile Gln Ile Pro Phe Met Arg Ala Ser Val Arg Glu Val Asp Leu Gln
        290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
            340                 345                 350

Gly Ala Ile Lys Val Gln Ile Gln Ser Leu Glu
        355                 360

<210> SEQ ID NO 14
<211> LENGTH: 1092
<212> TYPE: DNA
<213> ORGANISM: Artificial Sequence
<220> FEATURE:
<223> OTHER INFORMATION: Mutant

<400> SEQUENCE: 14
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc ccaagtcat ctgcaatgcc tgcgagccct gcctgactgg ccgttacaac     360
ggatgcgagc gcgttgactt cctctctacg cccctgtgc ccggccttct ccgccgctac     420
gttaaccacc ctgccgtgtg gtgccacaaa atcggtaaca tgtcctatga aacggtgcc     480 atgctcgagc ccctttccgt ggcgctggcc ggtcttcaga gagccggtgt tcgtctgggc     540
gaccctgtcc tcatctgtgg tgccggcccc gtcggtctga tcaccatgct ctgcgccaag     600

```
gccgctggtg cctgccctct tgtcattacc gacattgacg aaggccgctt gaagttcgcc    660
aaggagatct gccccgaggt cgtcacccac aaggtcgagc gcctgtcggc cgaggagtcg    720
gccaagaaga tcgtcgagag ctttggtgga atcgagcccg cggtggctct cgagtgtact    780
ggtgtcgaga gcagtatcgc ggctgctatc tgggccgtca agttcggcgg caaggtgttc    840
gtcatcggcg tgggcaagaa cgagatccag attcctttca tgcgcgccag tgtgcgcgag    900
gtcgacctgc agttccagta ccgttactgc aacacttggc ccaggccat cgcctggtc    960 gagaatggcc tcgttgacct caccaggctg gtgacgcacc gtttcccgtt ggaggatgcg   1020
ctcaaggcgt cgagacggc gtcagacccc aagacgggtg ccatcaaggt gcagatccag   1080
agtctggagt aa                                                         1092
```

<210> SEQ ID NO 15
<211> LENGTH: 363
<212> TYPE: PRT
<213> ORGANISM: Artificial Sequence
<220> FEATURE:
<223> OTHER INFORMATION: Mutant

<400> SEQUENCE: 15

```
Met Ala Ser Ser Ala Ser Lys Thr Asn Ile Gly Val Phe Thr Asn Pro
 1               5                  10                  15

Gln His Asp Leu Trp Ile Ser Glu Ala Ser Pro Ser Leu Glu Ser Val
            20                  25                  30

Gln Lys Gly Glu Glu Leu Lys Glu Gly Glu Val Thr Val Ala Val Arg
        35                  40                  45

Ser Thr Gly Ile Cys Gly Ser Asp Val His Phe Trp Lys His Gly Cys
    50                  55                  60

Ile Gly Pro Met Ile Val Glu Cys Asp His Val Leu Gly His Glu Ser
65                  70                  75                  80

Ala Gly Glu Val Ile Ala Val His Pro Ser Val Lys Ser Ile Lys Val
                85                  90                  95

Gly Asp Arg Val Ala Ile Glu Pro Gln Val Ile Cys Asn Ala Cys Glu
            100                 105                 110

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ile Gly
            180                 185                 190

Leu Ile Thr Met Leu Cys Ala Lys Ala Ala Gly Ala Cys Pro Leu Val
        195                 200                 205

Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ile Trp Ala
            260                 265                 270
```

```
Val Lys Phe Gly Gly Lys Val Phe Leu Gly Val Gly Lys Asn Glu
        275                 280                 285

Ile Gln Ile Pro Phe Met Arg Ala Ser Val Arg Glu Val Asp Leu Gln
        290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
                340                 345                 350

Gly Ala Ile Lys Val Gln Ile Gln Ser Leu Glu
        355                 360

<210> SEQ ID NO 16
<211> LENGTH: 1092
<212> TYPE: DNA
<213> ORGANISM: Artificial Sequence
<220> FEATURE:
<223> OTHER INFORMATION: Mutant

<400> SEQUENCE: 16
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc cccaagtcat ctgcaatgcc tgcgagccct gcctgactgg ccgttacaac     360
ggatgcgagc gcgttgactt cctctctacg ccccctgtgc ccggccttct ccgccgctac     420
gttaaccacc ctgccgtgtg gtgccacaaa atcggtaaca tgtcctatga aacggtgcc      480 atgctcgagc ccctttccgt ggcgctggcc ggtcttcaga gagccggtgt tcgtctgggc     540
gaccctgtcc tcatctgtgg tgccggcccc attggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720
gccaagaaga tcgtcgagag ctttggtgga atcgagcccg cggtggctct cgagtgtact     780
ggtgtcgaga gcagtatcgc ggctgctatc tgggccgtca agttcggcgg caaggtgttc     840
gtcctcggcg tgggcaagaa cgagatccag attcctttca tgcgcgccag tgtgcgcgag     900
gtcgacctgc agttccagta ccgttactgc aacacttggc ccagggccat tcgcctggtc     960
gagaatggcc tcgttgacct caccaggctg gtgacgcacc gtttcccgtt ggaggatgcg    1020
ctcaaggcgt tcgagacggc gtcagacccc aagacgggtg ccatcaaggt gcagatccag    1080
agtctggagt aa                                                        1092
```